US012280264B2

(12) United States Patent
Liu et al.

(10) Patent No.: US 12,280,264 B2
(45) Date of Patent: Apr. 22, 2025

(54) STIMULATION SOURCE GENERATION CIRCUIT FOR NERVE STIMULATOR (71) Applicant: SCENERAY CO., LTD., Jiangsu (CN)

(72) Inventors: Bin Liu, Jiangsu (CN); Weiran Zhu, Jiangsu (CN)

(73) Assignee: SCENERAY CO., LTD., Jiangsu (CN)

( * ) Notice: Subject to any disclaimer, the term of this patent is extended or adjusted under 35 U.S.C. 154(b) by 456 days.

(21) Appl. No.: 17/769,392

(22) PCT Filed: Nov. 28, 2019

(86) PCT No.: PCT/CN2019/121537
§ 371 (c)(1),
(2) Date: Apr. 15, 2022

(87) PCT Pub. No.: WO2021/072925
PCT Pub. Date: Apr. 22, 2021

(65) Prior Publication Data
US 2023/0191140 A1 Jun. 22, 2023

(30) Foreign Application Priority Data
Oct. 18, 2019 (CN) .......................... 201910993254.0

(51) Int. Cl.
*H02M 3/158* (2006.01)
*A61N 1/378* (2006.01)
(52) U.S. Cl.
CPC .......... *A61N 1/3782* (2013.01); *H02M 3/158* (2013.01)
(58) Field of Classification Search
CPC .................................................. H02M 3/158
See application file for complete search history.

(56) References Cited

U.S. PATENT DOCUMENTS 5,312,439 A * 5/1994 Loeb ..................... A61N 1/04
607/116
12,015,301 B2 * 6/2024 Takamatsu ............ H02J 7/0063
(Continued)

FOREIGN PATENT DOCUMENTS

CN 101648053 B * 5/2012
CN 203984025 U 12/2014
(Continued)

OTHER PUBLICATIONS

Extended European Search Report in Application No. 19949164.8 dated Oct. 2, 2023, 10 pages.
(Continued)

*Primary Examiner* — Sisay G Tiku
(74) *Attorney, Agent, or Firm* — ArentFox Schiff LLP; Joseph M. Maraia; Marlo Schepper Grolnic (57) ABSTRACT Provided is a stimulation source generation circuit for a nerve stimulator. A power module supplies an input voltage. A boosting module boosts the input voltage and generates a stimulation source. A charge branch of the boosting module includes an inductor and a first MOS tube. A discharge circuit includes a second MOS tube and an output branch for outputting the stimulation source. An adjustment module outputs an operating frequency according to a magnitude of the stimulation source. The adjustment module is further connected to control ends of the first MOS tube and the second MOS tube and adjusts on or off of the first MOS tube and the second MOS tube according to the operating frequency. The first MOS tube and the second MOS tube cannot be turned on at the same time.

10 Claims, 2 Drawing Sheets

(56) References Cited

U.S. PATENT DOCUMENTS

| | | |
|---|---|---|
| 2005/0134246 A1 | 6/2005 | Tobita |
| 2007/0097719 A1* | 5/2007 | Parramon ............. H02M 3/155 |
| | | 363/72 |
| 2008/0097529 A1* | 4/2008 | Parramon .......... A61N 1/36125 |
| | | 607/2 |
| 2009/0069869 A1* | 3/2009 | Stouffer ............. A61N 1/37223 |
| | | 607/61 |
| 2010/0211132 A1* | 8/2010 | Nimmagadda ....... H02M 3/156 |
| | | 607/60 |
| 2011/0063021 A1 | 3/2011 | Yamashita et al. |
| 2015/0258340 A1* | 9/2015 | Parramon .......... A61N 1/36125 |
| | | 607/2 |
| 2016/0129269 A1* | 5/2016 | Nimmagadda .... A61N 1/37211 |
| | | 607/60 |
| 2016/0172889 A1* | 6/2016 | Kim .................. H02J 7/007182 |
| | | 320/107 |
| 2017/0113567 A1* | 4/2017 | Koketsu ................ B60L 15/007 |
| 2017/0340886 A1* | 11/2017 | Parramon ............. A61N 1/372 |
| 2018/0104498 A1* | 4/2018 | Nimmagadda ........ A61N 1/378 |
| 2019/0174717 A1* | 6/2019 | McFarland ................ G01L 1/20 |
| 2020/0086125 A1* | 3/2020 | Parramon ............ A61N 1/3756 |
| 2020/0235664 A1* | 7/2020 | Takei ................... H02M 7/537 |
| 2022/0317204 A1* | 10/2022 | Zhu .................... A61N 1/36125 |

FOREIGN PATENT DOCUMENTS

| | | | | |
|---|---|---|---|---|
| CN | 205017210 U | | 2/2016 | |
| CN | 105896984 A | | 8/2016 | |
| CN | 106899204 A | | 6/2017 | |
| CN | 207304839 U | * | 5/2018 | |
| CN | 210923786 U | * | 7/2020 | ......... A61N 1/36125 |
| CN | 116722814 A | * | 9/2023 | |
| EP | 3033147 B1 | * | 10/2019 | ......... A61N 1/36125 |
| KR | 20200116585 A | * | 10/2020 | |
| WO | WO-2008048321 A1 | * | 4/2008 | ............. A61N 1/025 |
| WO | WO-2013000121 A1 | * | 1/2013 | ............... A61N 1/08 |
| WO | WO-2015023359 A1 | * | 2/2015 | ......... A61N 1/36125 |
| WO | WO-2021244899 A1 | * | 12/2021 | ............... B60L 50/15 |

OTHER PUBLICATIONS

International Search Report from related PCT Application No. PCT/CN2019/121537, issued Jul. 6, 2020 (4 pages, 2 in English, 2 in Chinese).

\* cited by examiner

STIMULATION SOURCE GENERATION CIRCUIT FOR NERVE STIMULATOR

CROSS-REFERENCE TO RELATED APPLICATIONS

This application is a U.S. National Stage Application of PCT Application Serial No. PCT/CN2019/121537, filed Nov. 28, 2019, which claims priority to Chinese Patent Application No. 201910993254.0, filed Oct. 18, 2019, the disclosures of which are incorporated herein by reference in their entireties.

TECHNICAL FIELD

The present application relates to the technical field of medical equipment and, in particular, to a stimulation source generation circuit for a nerve stimulator.

BACKGROUND

In an implantable medical device, a nerve stimulator performs chronic electrical stimulation on target nerves so as to effectively control symptoms of functional neurological diseases and psychosis. The nerve stimulator is in contact with the human body through electrodes. However, the magnitude of the stimulus required by different human bodies varies greatly. However, now the nerve stimulator is battery powered and can only provide a voltage of 3.6 V. At present, a boost circuit is used for boosting the voltage of the battery, and the magnitude of the electrical stimulation is between 0.1 V and 10 V. If a supply voltage of a stimulation source is much greater than a voltage required by the stimulator, a large part of the energy is wasted.

Therefore, it is necessary to design a stimulation source generation circuit that can generate a stimulation source close to a stimulus magnitude.

SUMMARY

To solve one of the preceding problems, the present application provides a stimulation source generation circuit for a nerve stimulator. The stimulation source generation circuit includes a power module, a boosting module, and an adjustment module. The power module is configured to supply an input voltage. The boosting module is connected to the power module and configured to boost the input voltage and generate a stimulation source; where the boosting module includes a charge branch and a discharge branch, where the charge branch is connected in parallel with two ends of the power module and includes an inductor and a first MOS tube, the inductor is connected to a positive electrode of the power module, an input end of the first MOS tube is connected to another end of the inductor, and an output end of the first MOS tube is connected to a negative electrode of the power module; the discharge branch includes a second MOS tube and an output branch for outputting the stimulation source, an input end of the second MOS tube is connected to one end of the inductor facing away from the power module, an output end of the second MOS tube is connected to one end of the output branch, and another end of the output branch is connected to the negative electrode of the power module.

The adjustment module is connected to the output branch and configured to output an operating frequency according to a magnitude of the stimulation source; where the adjustment module is further connected to a control end of the first MOS tube and a control end of the second MOS tube and configured to adjust on or off of the first MOS tube and the second MOS tube according to the operating frequency; and only at most one of the first MOS tube or the second MOS tube is turned on at the same time.

In an embodiment of the present application, the power module includes a battery, an input capacitor connected in parallel with two ends of the battery, and a first switch connected between the battery and the input capacitor.

In an embodiment of the present application, the adjustment module further includes a first comparator branch, a frequency controller, and a first set voltage branch, where the frequency controller is communicatively connected to the control end of the first MOS tube and the control end of the second MOS tube; and the first comparator branch includes a first comparator, where an output end of the first comparator is connected to the frequency controller; and one of a positive input end or a negative input end of the first comparator is selectively connected to the output branch, and another one of the positive input end or the negative input end of the first comparator is connected to the first set voltage branch.

In an embodiment of the present application, the adjustment module further includes an oscillator and a driver that are communicatively connected to the frequency controller, the oscillator is connected to an input end of the driver, and an output end of the driver is connected to the control end of the first MOS tube and the control end of the second MOS tube.

In an embodiment of the present application, the output branch includes an output capacitor, two ends of the output capacitor are connected to the output end of the second MOS tube and the negative electrode of the power module, respectively, and the two ends of the output capacitor are used for outputting the stimulation source; the output branch further includes a voltage divider branch connected in parallel with the two ends of the output capacitor, the voltage divider branch includes a first resistor and a second resistor connected in series, and the first comparator is selectively connected between the first resistor and the second resistor.

In an embodiment of the present application, the stimulation source generation circuit includes a reference voltage module, where the reference voltage module is capable of generating a first set voltage; the first set voltage branch includes a first capacitor, where one end of the first capacitor is grounded; the first comparator branch further includes a first single pole double throw switch, where two movable ends of the first single pole double throw switch are connected to the output branch and the reference voltage module, respectively; the first comparator branch further includes a second switch, where the second switch is connected between the output end of the first comparator and one end of the first capacitor facing away from ground; and one of the positive input end or the negative input end of the first comparator is selectively connected to a stationary end of the first single pole double throw switch, and another one of the positive input end or the negative input end of the first comparator is connected to the one end of the first capacitor facing away from the ground.

In an embodiment of the present application, the stimulation source generation circuit further includes a first sampling module, the first sampling module includes a third resistor, a second comparator branch, and a second set voltage branch, and the third resistor is connected between the output end of the first MOS tube and the negative electrode of the power module; and the second comparator branch includes a second comparator, where an output end of the second comparator is connected to the driver; and one of a positive input end or a negative input end of the second comparator is selectively connected to the second set voltage branch, and another one of the positive input end or the negative input end of the second comparator is connected to one end of the third resistor facing away from the negative electrode of the power module.

In an embodiment of the present application, the stimulation source generation circuit includes a reference voltage module, where the reference voltage module is capable of generating a second set voltage; the second set voltage branch includes a second capacitor, where one end of the second capacitor is grounded; the second comparator branch further includes a second single pole double throw switch, where two movable ends of the second single pole double throw switch are connected to the reference voltage module and the one end of the third resistor facing away from the negative electrode of the power module, respectively; the second comparator further includes a third switch, and the third switch is connected to the output end of the second comparator and one end of the second capacitor facing away from ground; and one of the positive input end or the negative input end of the second comparator is connected to a stationary end of the second single pole double throw switch, and another one of the positive input end or the negative input end of the second comparator is connected to the one end of the second capacitor facing away from the ground.

In an embodiment of the present application, the stimulation source generation circuit further includes a second sampling module, the second sampling module includes a fourth resistor, a third comparator branch, and a third set voltage branch, and the fourth resistor is connected between the output end of the second MOS tube and the output branch; and the third comparator branch includes a third comparator, where an output end of the third comparator is connected to the driver; and a positive input end and a negative input end of the third comparator branch are connected in parallel with two ends of the fourth resistor.

In an embodiment of the present application, the third comparator branch further includes the third set voltage branch connected to a common-mode input end of the third comparator.

In an embodiment of the present application, the stimulation source generation circuit includes a reference voltage module, where the reference voltage module is capable of generating a third set voltage; and the third set voltage branch includes a third capacitor and a fourth switch, where one end of the third capacitor is grounded, and another end of the third capacitor is connected to the common-mode input end of the third comparator; one end of the fourth switch is connected to one end of the third capacitor facing away from ground, and another end of the fourth switch is connected to the reference voltage module.

Compared with the existing art, the boosting module in the present application is a boosting circuit, and the boosting circuit boosts the input voltage through the cooperation of the inductor, the first MOS tube and the second MOS tube. Moreover, the adjustment module monitors the stimulation source outputted by the output branch and outputs the operating frequency according to the magnitude of the stimulation source so that the first MOS tube and the second MOS tube are turned on or off with an appropriate operating frequency, and thus the stimulation source outputted by the output branch is within an appropriate range.

DETAILED DESCRIPTION

For a better understanding of solutions in the present application by those skilled in the art, the solutions in embodiments of the present application will be described clearly and completely in conjunction with the drawings in the embodiments of the present application. Apparently, the embodiments described below are part, not all, of embodiments. Based on the embodiments of the present application, other embodiments obtained by those of ordinary skill in the art on the premise that no creative work is done are within the scope of the present application.

Figure 1:
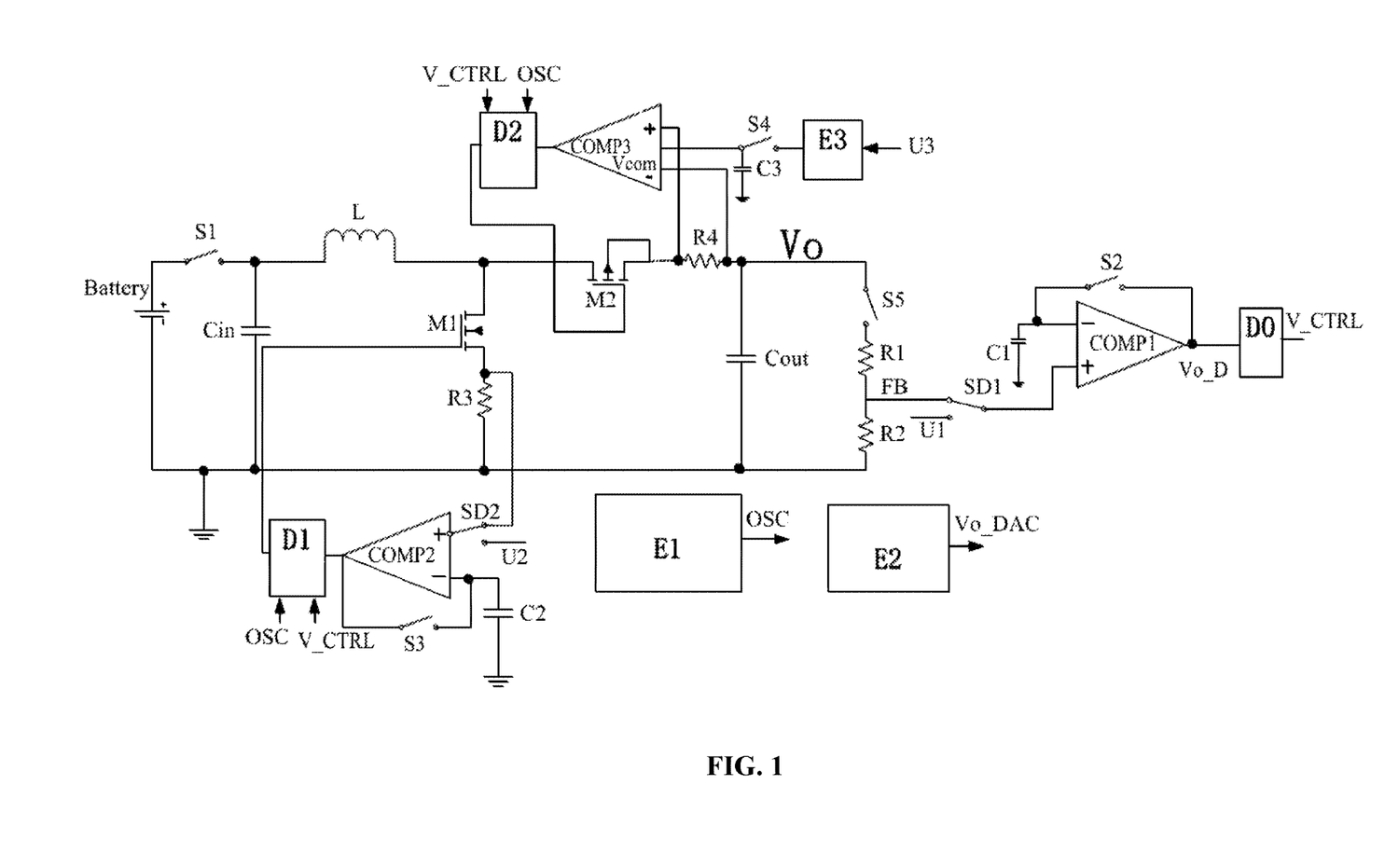
FIG. 1 is a circuit diagram of a stimulation source generation circuit according to the present application.
Figure 2:
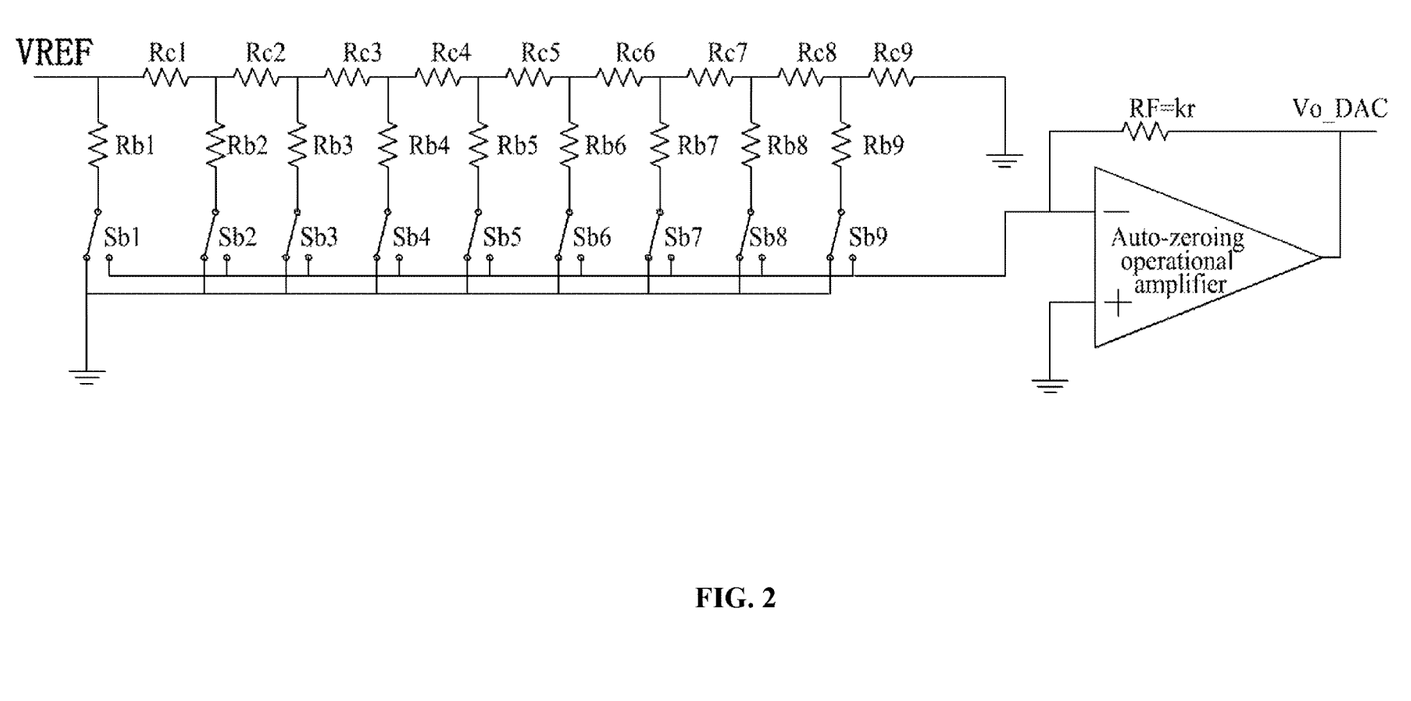
FIG. 2 is a circuit diagram of a reference voltage module according to the present application.

As shown in FIGS. 1 and 2, the present application provides a stimulation source Vo generation circuit for a nerve stimulator, and the stimulation source Vo generation circuit includes a power module, a boosting module, and an adjustment module.

The power module is configured to supply an input voltage.

The boosting module is connected to the power module and configured to boost the input voltage and generate a stimulation source Vo. The boosting module includes a charge branch and a discharge branch.

The charge branch is connected in parallel with two ends of the power module and includes an inductor L and a first MOS tube M1, the inductor L is connected to a positive electrode of the power module, an input end of the first MOS tube M1 is connected to the other end of the inductor L, an output end of the first MOS tube M1 is connected to a negative electrode of the power module, and the negative electrode of the power module is grounded.

The discharge branch includes a second MOS tube M2 and an output branch for outputting the stimulation source Vo, an input end of the second MOS tube M2 is connected to one end of the inductor L facing away from the power module, an output end of the second MOS tube M2 is connected to one end of the output branch, and the other end of the output branch is connected to the negative electrode of the power module.

The adjustment module is connected to the output branch and configured to output an operating frequency according to a magnitude of the stimulation source Vo. The adjustment module is further connected to a control end of the first MOS tube M1 and a control end of the second MOS tube M2 and configured to adjust on or off of the first MOS tube M1 and the second MOS tube M2 according to the operating frequency. Only at most one of the first MOS tube M1 or the second MOS tube M2 is turned on at the same time.

The boosting module in the present application is a boosting circuit, and the boosting circuit boosts the input voltage through the cooperation of the inductor L, the first MOS tube M1 and the second MOS tube M2. Moreover, the adjustment module monitors the stimulation source Vo outputted by the output branch and outputs the operating frequency according to the magnitude of the stimulation source Vo so that the first MOS tube M1 and the second MOS tube M2 are turned on or off with an appropriate operating frequency, and thus the stimulation source Vo outputted by the output branch is within an appropriate range.

In an embodiment, the boosting module is the boosting circuit. Therefore, when the first MOS tube M1 is turned on and the second MOS tube M2 is turned off, the power module, the inductor L, and the first MOS tube M1 form a charge loop, the current in the inductor L increases linearly in a certain proportion, and as the current increases, a certain amount of energy is also stored in the inductor L. When the first MOS tube M1 is turned off and the second MOS tube M2 is turned on, the power module, the inductor L, the second MOS tube M2, and the output branch form a discharge loop, the current in the inductor L flows to the output branch and gradually decreases, and the voltage on the inductor L is superimposed on the power module so that the voltage across the output branch is greater than the voltage across the power module, and correspondingly, the boost is completed. Therefore, the first MOS tube M1 and the second MOS tube M2 are frequently turned on and off so that an output voltage on the output branch can be gradually increased. Of course, when both the first MOS tube M1 and the second MOS tube M2 are turned off, the boosting module does not operate; and to ensure a normal operation of the boosting module, the first MOS tube M1 and the second MOS tube M2 cannot be turned on at the same time.

In addition, the power module further includes a battery, an input capacitor Cin connected in parallel with two ends of the battery, and a first switch S1 connected between the battery and the input capacitor Cin. When the first switch S1 is turned on, the input capacitor Cin takes power from the battery, and when the first switch S1 is turned off, the boosting module takes power from the input capacitor Cin. The first switch S1 is turn off or on in stages. This is since an internal resistance of the battery is too large. If the boosting module directly takes power from the battery, the efficiency is greatly reduced. Therefore, to improve the efficiency, the input capacitor Cin is used to supply the input voltage to the boosting module.

From the above, the adjustment module may monitor the stimulation source Vo outputted by the output branch and outputs the operating frequency according to the magnitude of the stimulation source Vo. The following is how the adjustment module monitors the stimulation source Vo and determines a voltage range of the stimulation source Vo.

The adjustment module further includes a first comparator branch, a frequency controller DO and a first set voltage branch, and the frequency controller DO is communicatively connected to the control end of the first MOS tube M1 and the control end of the second MOS tube M2 so that the frequency controller DO outputs a control signal and controls on and off of the first MOS tube M1 and the second MOS tube M2. Moreover, the first comparator branch includes a first comparator COMP1, where an output end of the first comparator COMP1 is connected to the frequency controller DO; and one of a positive input end and a negative input end of the first comparator COMP1 is selectively connected to the output branch, and the other one of the positive input end and the negative input end of the first comparator COMP1 is connected to the first set voltage branch. Therefore, the first comparator COMP1 compares the voltage on the output branch with a first set voltage U1 on the first set voltage branch and then outputs a comparison result to the frequency controller DO, and then the frequency controller DO is communicatively connected to the first MOS tube M1 and the second MOS tube M2 and controls the first MOS tube M1 and the second MOS tube M2.

The first comparator COMP1 is an operational amplifier, and in this embodiment, the negative input end of the first comparator COMP1 is connected to the first set voltage branch, and the positive input end of the first comparator COMP1 is selectively connected to the output branch. Therefore, when the voltage on the output branch is less than the first set voltage U1 on the first set voltage branch, an output result of the first comparator COMP1 is 0, and when the voltage on the output branch is greater than the first set voltage U1 on the first set voltage branch, the output result of the first comparator COMP1 is 1.

In addition, it is to be noted that, as mentioned above, the frequency controller DO is communicatively connected to the first MOS tube M1 and the second MOS tube M2. In this embodiment, the adjustment module further includes an oscillator E1 and a driver that are communicatively connected to the frequency controller DO so as to control a switching frequency of the first MOS tube M1 and a switching frequency of the second MOS tube M2. In an embodiment, the oscillator E1 is connected to an input end of the driver, and an output end of the driver is connected to the control end of the first MOS tube M1 and the control end of the second MOS tube M2.

As mentioned above, the adjustment module may control the on and off of the first MOS tube M1 and the second MOS tube M2 according to the magnitude of the stimulation source Vo. In an embodiment, the oscillator E1 generates the operating frequency, and the frequency controller DO is communicatively connected to the oscillator E1 so as to control, through a control signal, the oscillator E1 to output the operating frequency within an appropriate time period. The oscillator E1 is connected to the driver, the oscillator E1 outputs the operating frequency to the driver, and the driver adjusts the on and off of the first MOS tube M1 and the second MOS tube M2 based on the operating frequency. In this embodiment, the oscillator E1 and the frequency controller DO are both connected to the driver, and the driver is used as a communication medium of the oscillator E1 and the frequency controller DO to output signals to the first MOS tube M1 and the second MOS tube M2. Of course, if the frequency controller DO is connected to the oscillator E1 first and the oscillator E1 is then connected to the driver, the object of the present application may also be achieved.

Generally, the oscillator E1 may continuously generate a relatively large frequency. Therefore, in this embodiment, when the frequency controller DO determines that the output voltage is within an appropriate range, a determination result is outputted to the driver, and the driver receives the operating frequency generated by the oscillator E1 and sends the operating frequency to the control end of the first MOS tube M1 and the control end of the second MOS tube M2 so that the first MOS tube M1 and the second MOS tube M2 operate with a relatively large operating frequency, and the voltage of the stimulation source rapidly satisfies the requirements. When the output voltage is not within the appropriate range, the determination result is outputted to the driver, the driver does not receive the operating frequency generated by the oscillator E1 and turns off both the first MOS tube M1 and the second MOS tube M2, and the boosting module does not operate.

Since a voltage of the stimulation source Vo required to be outputted by the output branch is greater than a voltage of the first comparator COMP1, the stimulation source Vo and the first set voltage U1 are generally not directly compared. Therefore, the output branch generally includes an output capacitor Cout and a voltage divider branch connected in parallel with two ends of the output capacitor Cout. The two ends of the output capacitor Cout are connected to the output end of the second MOS tube M2 and the negative electrode of the power module, respectively, and the two ends of the output capacitor Cout are configured to store power and output the stimulation source Vo. In the case where the first MOS tube M1 and the second MOS tube M2 are frequently turned on and off, the power stored in the output capacitor Cout also increases gradually, and the voltage of the stimulation source Vo at the two ends of the output capacitor Cout also increases gradually. Correspondingly, a voltage on the voltage divider branch also increases gradually.

The voltage divider branch includes a first resistor R1 and a second resistor R2 connected in series, and the first comparator COMP1 is connected between the first resistor R1 and the second resistor R2. In this embodiment, the positive input end of the first comparator COMP1 is selectively connected between the first resistor R1 and the second resistor R2, and the second resistor R2 is connected to a negative electrode of the battery. Therefore, when the first comparator COMP1 performs comparison, the first comparator COMP1 compares a divided voltage on the second resistor R2 and the first set voltage U1. Moreover, in this embodiment, a resistance of the first resistor R1 is four times a resistance of the second resistor R2 so that the divided voltage on the second resistor R2 is one fifth of the voltage of the stimulation source Vo. It is to be noted that when the positive input end of the first comparator COMP1 is connected between the first resistor R1 and the second resistor R2, the first comparator COMP1 is used as a comparator.

Moreover, the voltage divider branch further includes a fifth switch S5, and the fifth switch S5 is connected in series with the first resistor R1 and the second resistor R2. Only when the fifth switch S5 is connected, the current flows through the voltage divider branch, and the following adjustment module operates. After the nerve stimulator starts to operate, the fifth switch S5 is disconnected, and the stimulation source is outputted outward through the output capacitor Cout.

As described above, the first set voltage branch may output the first set voltage U1, and how the first set voltage branch stores the first set voltage U1 is described below in detail.

The stimulation source Vo generation circuit further includes a reference voltage module E2, where the reference voltage module E2 is capable of generating the first set voltage U1. The first set voltage branch includes a first capacitor C1, and one end of the first capacitor C1 is grounded. The first comparator branch further includes a first single pole double throw switch SD1, and two movable ends of the first single pole double throw switch SD1 are connected to the output branch and the reference voltage module E2, respectively. The first comparator branch further includes a second switch S2, the second switch S2 is connected between the output end of the first comparator COMP1 and one end of the first capacitor C1 facing away from the ground. One of the positive input end and the negative input end of the first comparator COMP1 is selectively connected to a stationary end of the first single pole double throw switch SD1, and the other one of the positive input end and the negative input end of the first comparator COMP1 is connected to the end of the first capacitor C1 facing away from the ground.

In this embodiment, the negative input end of the first comparator COMP1 is connected to the first capacitor C1, and the positive input end of the first comparator COMP1 is connected to the stationary end of the first single pole double throw switch SD1. The two movable ends of the first single pole double throw switch SD1 are connected between the first resistor R1 and the second resistor R2, and to the reference voltage module E2, respectively. Before the first comparator COMP1 starts to perform comparison, the second switch S2 is connected first so that the first comparator branch forms a follower circuit. Moreover, the first single pole double throw switch SD1 is connected to the reference voltage module E2 so that since the first comparator branch forms the follower circuit, the first set voltage U1 outputted from the reference voltage module E2 may be transmitted to the first capacitor C1. Then, the second switch S2 is disconnected, and the first single pole double throw switch SD1 is connected between the first resistor R1 and the second resistor R2 so that comparison between the divided voltage on the second resistor R2 and the first set voltage U1 may be performed.

When the divided voltage on the second resistor R2 is less than the first set voltage U1, the first comparator COMP1 outputs 0, and the frequency controller DO outputs a signal to make the first MOS tube M1 and the second MOS tube M2 to operate with the operating frequency. When the divided voltage on the second resistor R2 is greater than the first set voltage U1, the first comparator COMP1 outputs 1, and the frequency controller DO outputs a signal that makes the first MOS tube M1 and the second MOS tube M2 not operate.

As mentioned above, the frequency controller DO is communicatively connected to the oscillator E1 and the driver. The operating frequency generated by the oscillator E1 is relatively large, which is generally 100 kHz, and the relatively large operating frequency may make the stimulation source Vo rapidly satisfy requirements of the first set voltage U1. Moreover, the first MOS tube M1 and the second MOS tube M2 need to be controlled respectively by two drivers in actual work. Therefore, in fact, the driver includes a first driver D1 and a second driver D2, where the first driver D1 controls the first MOS tube M1, and the second driver D2 controls the second MOS tube M2.

The preceding is a detailed description in which the first comparator COMP1 circuit controls the operating frequency of the first MOS tube M1 and the operating frequency of the second MOS tube M2. The following describes the on and off of the first MOS tube M1 and the second MOS tube M2.

The stimulation source Vo circuit further includes a first sampling module, and the first sampling module is configured to determine a current in the charge loop so as to prevent the current in the charge loop from being too large and prevent the power stored in the inductor L from being too large. In an embodiment, the first sampling module includes a third resistor R3, a second comparator COMP2 branch, and a second set voltage branch, and the third resistor R3 is connected between the output end of the first MOS tube M1 and the negative electrode of the power module. The third resistor R3 is used as a sampling resistor, which is convenient for the first sampling module to determine the current in the charge loop.

The second comparator branch includes a second comparator COMP2, where the driver is the first driver D1, and an output end of the second comparator COMP2 is connected to the first driver D1. One of a positive input end and a negative input end of the second comparator COMP2 is selectively connected to the second set voltage branch, and the other one of the positive input end and the negative input end of the second comparator COMP2 is connected to one end of the third resistor R3 facing away from the negative electrode of the power module. In this embodiment, the positive input end of the second comparator COMP2 is selectively connected to the third resistor R3, and the negative input end of the second comparator COMP2 is connected to the second set voltage branch. When a voltage on the third resistor R3 is less than a second set voltage U2 on the second set voltage branch, the second comparator COMP2 outputs 0, and when the voltage on the third resistor R3 is greater than the second set voltage U2 on the second set voltage branch, the second comparator COMP2 outputs 1.

Moreover, the output end of the second comparator COMP2 is directly connected to the first driver D1. Therefore, in this embodiment, only when the voltage on the third resistor R3 is lower than the second set voltage U2, the first driver D1 may operate and receive the operating frequency generated by the oscillator E1 and a control signal generated by the frequency controller D0 so as to make the first MOS tube M1 operate. When the voltage on the third resistor R3 is higher than the second set voltage U2, the first driver D1 directly controls the first MOS tube M1 to be turned off. Therefore, the control of the second comparator COMP2 is prioritized over the control of the operating frequency by the oscillator E1. During the operation of the boosting module, the first MOS tube M1 is turned on and off at the operating frequency. However, if the current in the charge loop is too large, the first MOS tube M1 is immediately turned off to wait for the next turn-on.

Similarly, as described above, the negative input end of the second comparator COMP2 is connected to the second set voltage branch for determination. In an embodiment, the reference voltage module E2 may also generate the second set voltage U2, and the second set voltage branch includes a second capacitor C2, where one end of the second capacitor C2 is grounded, and the other end of the second capacitor C2 is connected to the first comparator COMP1.

The second comparator branch further includes a second single pole double throw switch SD2. Two movable ends of the second single pole double throw switch SD2 are connected to the reference voltage module E2 and the end of the third resistor R3 facing away from the negative electrode of the power module. The second comparator COMP2 further includes a third switch S3, and the third switch S3 is connected to the output end of the second comparator COMP2 and one end of the second capacitor C2 facing away from ground.

One of the positive input end and the negative input end of the second comparator COMP2 is connected to a stationary end of the second single pole double throw switch SD2, and the other one of the positive input end and the negative input end of the second comparator COMP2 is connected to the end of the second capacitor C2 facing away from the ground. As mentioned above, the positive input end of the second comparator COMP2 is connected to the stationary end of the second single pole double throw switch SD2, the negative input end of the second comparator COMP2 is connected to the second capacitor C2, and the third switch S3 is also connected between the output end and the negative input end of the second comparator COMP2. Before the first comparator COMP1 starts to perform comparison, the third switch S3 is connected first so that the second comparator COMP2 branch forms a follower circuit. Moreover, the second single pole double throw switch SD2 is connected to the reference voltage module E2 so that since the second comparator COMP2 branch forms the follower circuit, the second set voltage U2 outputted from the reference voltage module E2 may be transmitted to the second capacitor C2. Then, the third switch S3 is disconnected, and the first single pole double throw switch SD1 is connected to the third resistor R3 so that comparison between a divided voltage on the third resistor R3 and the second set voltage U2 may be performed.

When the divided voltage on the third resistor R3 is less than the second set voltage U2, the second comparator COMP2 outputs 0, and the first driver D1 operates so that the first driver D1 may receive a control signal and the operating frequency, and the first MOS tube M1 may operate with the operating frequency. When the divided voltage on the third resistor R3 is greater than the second set voltage U2, the second comparator COMP2 outputs 1, the first driver D1 does not operate, and the first MOS tube M1 is turned off and does not operate.

Therefore, through the preceding circuit settings, the following can be avoided: when the boosting module operates, the current passing through the inductor L in the charge loop is too large, and the energy stored in the inductor L is too large.

Similarly, a second sampling module is disposed in the discharge loop.

In an embodiment, the second sampling module includes a fourth resistor R4, a third comparator branch, and a third set voltage U3 module, and the fourth resistor R4 is connected between the output end of the second MOS tube M2 and the output branch so that the second sampling module may be configured to sample the current in the discharge loop.

The third comparator branch includes a third comparator COMP3, the driver is the second driver D2, and an output end of the third comparator COMP3 is connected to the second driver D2. A positive input end and a negative input end of the third comparator branch are connected to two ends of the fourth resistor R4, respectively, so that the third comparator COMP3 may be configured to determine a current flow of the fourth resistor R4. In this embodiment, the positive input end of the third comparator COMP3 is connected to one end of the fourth resistor R4 connected to an output module, and the negative input end of the third comparator COMP3 is connected to the output end of the second MOS transistor M2. Therefore, when the current in the fourth resistor R4 is a normal current, the current flows from the inductor to the output module, and the third comparator COMP3 outputs 1; otherwise, the third comparator COMP3 outputs 0.

In an embodiment, in the case of the discharge loop, the current in the inductor L is transferred to the output capacitor Cout. If the current in the inductor L is transferred completely, the situation that the power of the output capacitor Cout returns to the inductor L again may appear.

Therefore, it is necessary to turn off the second MOS tube M2 in the case where the current in the discharge loop reaches 0, so as to prevent the current from flowing backward and affecting the efficiency of the circuit.

Moreover, since the output end of the third comparator COMP3 is connected to the second driver D2, the control of the third comparator COMP3 is prioritized over the control of the operating frequency by the second driver D2. During the operation of the boosting module, the second MOS tube M2 is turned on and off at the operating frequency. However, if the current in the discharge loop reaches 0 or is about to reach 0, the first MOS tube M1 is immediately turned off to wait for the next turn-on.

However, the existing comparator, even a high-speed comparator, has a delay of several hundreds of nanoseconds. Therefore, a delay compensation must be made for the high-speed comparator so that the third comparator COMP3 is turned over before it is detected that the current in the discharge loop is reduced to 0, and thus the second MOS tube M2 is turned off. Therefore, the third comparator branch further includes the third set voltage U3 module connected to a common-mode input end Vcom of the third comparator COMP3. The third set voltage U3 module may change a common-mode input voltage of the third comparator COMP3 so that the third comparator COMP3 is turned over before the current in the discharge loop is reduced to 0.

Similarly, the third set voltage U3 module may output a third set voltage U3, and the reference voltage module E2 may generate the third set voltage U3. The third set voltage U3 module includes a third capacitor C3 and a fourth switch S4, where one end of the third capacitor C3 is grounded, and the other end of the third capacitor C3 is connected to the common-mode input end Vcom of the third comparator COMP3. One end of the fourth switch S4 is connected to one end of the third capacitor C3 facing away from ground, and the other end of the fourth switch S4 is connected to the reference voltage module E2. In this embodiment, the stimulation source generation circuit further includes a delay optimization module E3, where the delay optimization module E3 is connected between the fourth switch S4 and the reference voltage module E2.

Therefore, when the fourth switch S4 is connected, the third set voltage U3 outputted by the reference voltage module E2 enters the third capacitor C3. After the fourth switch S4 is disconnected, the third comparator COMP3 can start to perform comparison. Therefore, with the preceding arrangement, in the case where a voltage across the fourth resistor R4 is about to drop to 0, the third comparator COMP3 may be turned over and the second MOS transistor M2 may be turned off so as to prevent current inversion in the discharge loop.

Moreover, the reference voltage module E2 may generate the first set voltage U1, the second set voltage U2, and the third set voltage U3, and the first set voltage U1, the second set voltage U2, and the third set voltage U3 is finely adjustable. In an embodiment, FIG. 2 shows the reference voltage module E2, the reference voltage module E2 includes a fourth comparator COMP4, where an output end and a negative input end of the fourth comparator COMP4 are connected through a feedback resistor RF, the output end of the fourth comparator COMP4 outputs a reference output voltage Vo_DAC, and a positive input end of the fourth comparator COMP4 is grounded. The negative input end of the fourth comparator COMP4 is further connected to a resistance module. The reference output voltage Vo_DAC is the first set voltage U1, the second set voltage U2, and the third set voltage U3.

The resistance module includes a reference input voltage VREF and multiple reference resistors. In an embodiment, the reference resistors include a first reference resistor Rb1 to a ninth reference resistor Rb9, a first distribution resistor Rc1 to a ninth distribution resistor Rc9, and a first reference single pole double throw switch Sb1 to a ninth reference single pole double throw switch Sb9. One end of the first reference resistor Rb1 is connected to the reference input voltage VREF, and the other end of the first reference resistor Rb1 is connected to a stationary end of the first reference single pole double throw switch Sb1. One end of the first distribution resistor Rc1 is connected to one end of the first reference resistor Rb1, the other end of the first distribution resistor Rc1 is connected to the second reference resistor Rb2, and the other end of the second reference resistor Rb2 is connected to a stationary end of the second reference single pole double throw switch Sb2. Correspondingly, one end of the second distribution resistor Rc2 is connected between the second reference resistor Rb2 and the first distribution resistor Rc1, the other end of the second distribution resistor Rc2 is connected to the third reference resistor Rb3, and the other end of the third reference resistor Rb3 is connected to a stationary end of the third single pole double throw switch Sb3. By analogy, then, one end of the ninth distribution resistor Rc9 is connected between the eighth distribution resistor Rc8 and the ninth reference resistor Rb9, and the other end of the ninth distribution resistor Rc9 is grounded. Moreover, one of movable ends of each of the first reference single pole double throw switch Sb1 to the ninth reference single pole double throw switch Sb9 is grounded, and the other movable ends of the first reference single pole double throw switch Sb1 to the ninth reference single pole double throw switch Sb9 are connected to each other and connected to the negative input end of the fourth comparator COMP4.

In addition, in this embodiment, resistances of the first reference resistor Rb1 to the ninth reference resistor Rb9 are all set to be 2r, resistances of the first distribution resistor Rc1 to the eighth distribution resistor Rc8 are all set to be r, a resistance of the ninth distribution resistor Rc9 is set to be 2r, and a resistance of the feedback resistor RF is set to be kr. Therefore, a relationship between the reference output voltage Vo_DAC, the reference input voltage VREF and the resistance module is described below.

$$V_o\_DAC = VREF * \left( b_1 * \frac{1}{2} + b_2 * \frac{1}{2^2} + b_3 * \frac{1}{2^3} + \ldots + b_9 * \frac{1}{2^9} \right)$$

b1 to b9 denote on and off conditions of the first reference single pole double throw switch Sb1 to the ninth reference single pole double throw switch Sb9. For example, when the first reference single pole double throw switch Sb1 is connected to the ground, b1 is 0, and when the first reference single pole double throw switch Sb1 is connected to the negative input end of the fourth comparator COMP4, b1 is 1. Therefore, it can be seen from the preceding formula that an output range of the reference output voltage Vo_DAC is accurate to $1/2^9$, so the reference circuit may output a precisely adjustable reference output voltage Vo_DAC. Values of the first set voltage U1, the second set voltage U2, and the third set voltage U3 may also be precisely adjustable.

Of course, the nerve stimulator circuit also has a corresponding operating method. Although the circuit is basically automatically controlled by the first comparator COMP1, the second comparator COMP2, the third comparator COMP3 and the like to form the stimulation source Vo, since settings of the first set voltage U1, the second set voltage U2, and the third set voltage U3 are involved, the preceding first switch S1 to the fifth switches S5, the first single pole double throw switch SD1, and the second single pole double throw switch SD2 all need to be controlled.

Therefore, the operating method of the stimulation source Vo generation circuit for a nerve stimulator includes steps described below.

The first capacitor C1 is controlled to store the first set voltage U1, the second capacitor C2 is controlled to store the second set voltage U2, and the third capacitor C3 is controlled to store the third set voltage U3.

The first switch S1 is connected for a duration of T1 and then disconnected.

The first single pole double throw switch SD1 is controlled to be connected between the first resistor R1 and the second resistor R2, and the second single pole double throw switch SD2 is controlled to be connected to the third resistor R3.

The fifth switch S5 is disconnected.

Nerve stimulation is started.

Corresponding to the above, after the first switch S1 is connected, the battery charges the input capacitor Cin. After the input capacitor Cin is charged for the duration of T1, the first switch S1 is disconnected, and a certain amount of power is stored in the input capacitor Cin.

The first single pole double throw switch SD1 is connected between the first resistor R1 and the second resistor R2, and after the second single pole double throw switch SD2 is connected to the third resistor R3, the first comparator COMP1 starts to compare the first set voltage U1 and the voltage on the second resistor R2 so that the frequency controller DO outputs a control signal to make the first MOS tube M1 and the second MOS tube M2 operate. Moreover, in a single operation of the first MOS tube and the second MOS tube, the second comparator COMP2 compares the second set voltage U2 and the voltage on the third resistor R3, thereby determining whether the current in the charge loop is too large, The third comparator COMP3 also determines whether a magnitude of the current in the fourth resistor R4 is or is about to drop to 0 so that the third comparator COMP3 may be turned over in time, thereby preventing the current from flowing backward.

When the voltage on the second resistor R2 of the first comparator COMP1 is greater than or equal to the second set voltage U2, it means that the voltage of the stimulation source Vo reaches an appropriate range, and the frequency controller DO outputs the control signal to make both the first MOS tube M1 and the second MOS tube M2 to be turned off.

The fifth switch S5 is disconnected again so that the first comparator COMP1 does not operate.

The preceding step of controlling the first capacitor C1 to store the first set voltage U1, controlling the second capacitor C2 to store the second set voltage U2, and controlling the third capacitor C3 to store the third set voltage U3 includes steps described below.

The reference voltage module is controlled to generate the first set voltage U1.

The first single pole double throw switch SD1 is controlled to switch to be connected to the reference voltage module, and the second switch S2 is connected for a duration of T2.

The first single pole double throw switch SD1 and the second switch S2 are disconnected.

The reference voltage module is controlled to generate the second set voltage U2.

The second single pole double throw switch SD2 is controlled to switch to be connected to the reference voltage module, and the third switch S3 is connected for a duration of T3.

The second single pole double throw switch SD2 and the third switch S3 are disconnected.

The reference voltage module is controlled to generate the third set voltage U3.

The fourth switch S4 is connected for a duration of T4.

The fourth switch S4 is disconnected.

To sum up, in the present application, the boosting circuit is provided in the stimulation source generation circuit, the adjustment module is provided in the stimulation source generation circuit to monitor the stimulation source Vo outputted by the output branch and output the operating frequency according to the magnitude of the stimulation source Vo so that the first MOS tube M1 and the second MOS tube M2 are controlled to be turned on or off at an appropriate operating frequency, and thus the stimulation source Vo outputted by the output branch is within an appropriate range. Secondly, in the present application, in the adjustment branch, the first comparator compares the divided voltage on the output branch with the first set voltage U1, and the oscillator is controlled to generate a relatively high operating frequency when the divided voltage does not reach the first set voltage U1 so that the entire stimulation source generation circuit reach an appropriate value quickly. Moreover, after the divided voltage reaches the first set voltage U1, the first MOS tube M1, the second MOS tube M2, and the fifth switch S5 are immediately turned off so that the stimulation source generation circuit is disconnected, and thus the voltage of the stimulation source is kept on the output capacitor Cout. Furthermore, currents on the charge loop and the discharge loop are monitored through the first sampling circuit and the second sampling circuit, and the first MOS tube M1 and the second MOS tube M2 are turned off under appropriate circumstances so that the current in the charge loop does not become too large, and the current in the discharge loop does not flow backward.

In addition, in the present application, the power module includes the battery and the input capacitor, and the battery and the capacitor are charged before the boost starts so that after the boost starts, the boosting circuit takes power from the input capacitor, thereby reducing an internal resistance of the power module and improving efficiency.

Additionally, it is to be understood that although this specification is described in terms of the embodiments, not every embodiment includes only one independent solution. Such description mode of the specification is merely for the sake of clarity, and those skilled in the art should regard the specification as a whole. The solutions in the embodiments may also be appropriately combined to form other embodiments which are understood by those skilled in the art.

The series of detailed descriptions listed above are merely specific descriptions of feasible embodiments of the present application and are not intended to limit the protection scope of the present application. Any equivalent embodiments or variations made without departing from the technical spirit of the present application should be included within the protection scope of the present application.

What is claimed is:
1. A stimulation source generation circuit for a nerve stimulator, comprising:
 a power module,
 a boosting module, and
 an adjustment module;
 wherein the power module is configured to supply an input voltage;
 wherein the boosting module is connected to the power module and is configured to boost the input voltage and generate a stimulation source;
 wherein the boosting module comprises a charge branch and a discharge branch, wherein the charge branch is connected in parallel with two ends of the power module and comprises an inductor and a first MOS tube, one end of the inductor is connected to a positive electrode of the power module, another end of the inductor is connected to an input end of the first MOS tube, and an output end of the first MOS tube is connected to a negative electrode of the power module;
 wherein the discharge branch comprises a second MOS tube and an output branch for outputting the stimulation source, an input end of the second MOS tube is connected to the another end of the inductor, an output end of the second MOS tube is connected to one end of the output branch, and the another end of the output branch is connected to the negative electrode of the power module;

wherein the adjustment module is connected to the output branch and is configured to output an operating frequency according to a magnitude of the stimulation source;

wherein the adjustment module is further connected to a control end of the first MOS tube and a control end of the second MOS tube and is configured to adjust on or off of the first MOS tube and the second MOS tube according to the operating frequency and only at most one of the first MOS tube or the second MOS tube is turned on at a same time;

wherein the adjustment module further comprises a first comparator branch, a frequency controller, and a first set voltage branch, the frequency controller communicatively connected to the control end of the first MOS tube and the control end of the second MOS tube; and wherein the first comparator branch comprises a first comparator, an output end of the first comparator connected to the frequency controller, one of a positive input end or a negative input end of the first comparator selectively connected to the output branch, and another one of the positive input end or the negative input end of the first comparator connected to the first set voltage branch.

2. The stimulation source generation circuit of claim 1, wherein the power module comprises a battery, an input capacitor connected in parallel with two ends of the battery, and a first switch connected between the battery and the input capacitor.

3. The stimulation source generation circuit of claim 1, wherein the adjustment module further comprises an oscillator and a driver that are communicatively connected to the frequency controller, the oscillator is connected to an input end of the driver, and an output end of the driver is connected to the control end of the first MOS tube and the control end of the second MOS tube.

4. The stimulation source generation circuit of claim 3, further comprising a first sampling module, wherein the first sampling module comprises a third resistor, a second comparator branch, and a second set voltage branch, one end of the third resistor is connected to the negative electrode of the power module and another end of the third resistor is connected to the output end of the first MOS tube;

wherein the second comparator branch comprises a second comparator, and an output end of the second comparator is connected to the driver; and wherein one of a positive input end or a negative input end of the second comparator is selectively connected to the second set voltage branch, and another one of the positive input end or the negative input end of the second comparator is connected to the another end of the third resistor.

5. The stimulation source generation circuit of claim 4, further comprising a reference voltage module capable of generating a second set voltage;

wherein the second set voltage branch comprises a second capacitor, and one end of the second capacitor is grounded;

wherein the second comparator branch further comprises a second single pole double throw switch, and two movable ends of the second single pole double throw switch are connected to the reference voltage module and the another end of the third resistor, respectively;

wherein the second comparator further comprises a third switch connected to the output end of the second comparator and another end of the second capacitor; and wherein one of the positive input end or the negative input end of the second comparator is connected to a stationary end of the second single pole double throw switch, and another one of the positive input end or the negative input end of the second comparator is connected to the another end of the second capacitor.

6. The stimulation source generation circuit of claim 3, further comprising a second sampling module, wherein the second sampling module comprises a fourth resistor, a third comparator branch, and a third set voltage branch, and the fourth resistor is connected between the output end of the second MOS tube and the output branch; and the third comparator branch comprises a third comparator, and an output end of the third comparator is connected to the driver; and a positive input end and a negative input end of the third comparator branch are connected in parallel with two ends of the fourth resistor.

7. The stimulation source generation circuit of claim 6, wherein the third comparator branch further comprises the third set voltage branch connected to a common-mode input end of the third comparator.

8. The stimulation source generation circuit of claim 7, further comprising a reference voltage module capable of generating a third set voltage;

wherein the third set voltage branch comprises a third capacitor and a fourth switch, and one end of the third capacitor is grounded, and another end of the third capacitor is connected to the common-mode input end of the third comparator; and wherein one end of the fourth switch is connected to the another end of the third capacitor, and another end of the fourth switch is connected to the reference voltage module.

9. The stimulation source generation circuit of claim 1, wherein the output branch comprises an output capacitor, two ends of the output capacitor are connected to the output end of the second MOS tube and the negative electrode of the power module, respectively, and the two ends of the output capacitor are used for outputting the stimulation source; the output branch further comprises a voltage divider branch connected in parallel with the two ends of the output capacitor, the voltage divider branch comprises a first resistor and a second resistor connected in series, and the first comparator is selectively connected between the first resistor and the second resistor.

10. The stimulation source generation circuit of claim 1, further comprising a reference voltage module capable of generating a first set voltage;

wherein the first set voltage branch comprises a first capacitor, and one end of the first capacitor is grounded;

wherein the first comparator branch further comprises a first single pole double throw switch, and two movable ends of the first single pole double throw switch are connected to the output branch and the reference voltage module, respectively;

wherein the first comparator branch further comprises a second switch, and the second switch is connected between the output end of the first comparator and another end of the first capacitor; and wherein one of the positive input end or the negative input end of the first comparator is selectively connected to a stationary end of the first single pole double throw switch, and another one of the positive input end or the negative input end of the first comparator is connected to the another end of the first capacitor.

\* \* \* \* \*